US010932666B2

(12) United States Patent
Park et al.

(10) Patent No.: US 10,932,666 B2
(45) Date of Patent: Mar. 2, 2021

(54) METHOD AND APPARATUS FOR TRANSMITTING/RECEIVING HEALTH INFORMATION USING HUMAN BODY COMMUNICATION

(71) Applicant: Samsung Electronics Co., Ltd., Gyeonggi-do (KR)

(72) Inventors: Jae-Hyun Park, Seoul (KR); Jun-Ho Koh, Gyeonggi-do (KR); Seong-Jun Song, Gyeonggi-do (KR); Sang-Ho Lee, Gyeonggi-do (KR); Yong-Chan Lee, Seoul (KR); Jae-Ho Jung, Gyeonggi-do (KR)

(73) Assignee: Samsung Electronics Co., Ltd

( * ) Notice: Subject to any disclaimer, the term of this patent is extended or adjusted under 35 U.S.C. 154(b) by 0 days.

(21) Appl. No.: 15/378,969

(22) Filed: Dec. 14, 2016

(65) Prior Publication Data

US 2017/0164834 A1 Jun. 15, 2017

(30) Foreign Application Priority Data

Dec. 14, 2015 (KR) .................. 10-2015-0178487

(51) Int. Cl.
*A61B 5/00* (2006.01)
*G16H 40/63* (2018.01)
(52) U.S. Cl.
CPC .......... *A61B 5/0028* (2013.01); *A61B 5/4839* (2013.01); *A61B 5/6833* (2013.01); *A61B 5/6843* (2013.01); *G16H 40/63* (2018.01)

(58) Field of Classification Search
CPC ..... A61B 5/0024; A61B 5/0028; A61B 5/053; A61B 5/4839; A61B 2562/0209; A61B 5/6833; A61B 5/6843; G16H 40/63
See application file for complete search history.

(56) References Cited

U.S. PATENT DOCUMENTS 8,027,293 B2 * 9/2011 Spaur .................. H04L 12/5692
370/322
8,535,223 B2 9/2013 Corroy et al.
9,444,818 B2 * 9/2016 Lietz ...................... H04L 63/10
(Continued)

FOREIGN PATENT DOCUMENTS

CN 101073494 11/2007
CN 102065757 5/2011
(Continued)

OTHER PUBLICATIONS

International Search Report dated Mar. 30, 2017 issued in counterpart application No. PCT/KR2016/014663, 12 pages.
(Continued)

*Primary Examiner* — Franklin D Balseca
(74) *Attorney, Agent, or Firm* — The Farrell Law Firm, P.C.

(57) ABSTRACT

An electronic device and a method for transmitting health information by the electronic device are provided. The method includes receiving, from a terminal, a first message requesting the health information; measuring a body condition, in response the first message; and transmitting, to the terminal, a second message including the health information by using human body communication, the health information being based on the measured body condition.

8 Claims, 11 Drawing Sheets

(56) References Cited

U.S. PATENT DOCUMENTS

| | | | |
|---|---|---|---|
| 9,667,316 B2* | 5/2017 | Nguyen | H04B 3/54 |
| 9,853,743 B2* | 12/2017 | Schmidt | H04B 17/318 |
| 2006/0097892 A1* | 5/2006 | Zigdon | H04B 1/707 |
| | | | 340/870.02 |
| 2008/0262376 A1* | 10/2008 | Price | A61B 5/445 |
| | | | 600/547 |
| 2009/0022095 A1 | 10/2009 | Spaur et al. | |
| 2009/0264714 A1* | 10/2009 | Chou | A61B 5/0002 |
| | | | 600/301 |
| 2010/0136906 A1 | 6/2010 | Hwang et al. | |
| 2011/0087300 A1* | 4/2011 | Van Den Eerenbeemd | |
| | | | A63F 13/28 |
| | | | 607/2 |
| 2011/0295560 A1 | 12/2011 | Crockford | |
| 2012/0013446 A1 | 1/2012 | Ino | |
| 2012/0032778 A1* | 2/2012 | Nakano | G07C 9/00087 |
| | | | 340/5.52 |
| 2012/0126944 A1* | 5/2012 | Ueno | G07C 9/37 |
| | | | 340/5.82 |
| 2012/0330556 A1* | 12/2012 | Shaanan | A61B 5/145 |
| | | | 702/19 |
| 2013/0060098 A1 | 3/2013 | Thomsen et al. | |
| 2014/0308898 A1* | 10/2014 | Lee | H04W 76/14 |
| | | | 455/41.3 |
| 2015/0178581 A1* | 6/2015 | Aoki | G06K 9/00087 |
| | | | 382/115 |
| 2015/0217052 A1 | 8/2015 | Keenan et al. | |
| 2015/0318933 A1 | 11/2015 | Washiro et al. | |
| 2017/0173261 A1* | 6/2017 | O'Connor | A61M 5/1723 |

FOREIGN PATENT DOCUMENTS

| | | |
|---|---|---|
| CN | 104854802 | 8/2015 |
| CN | 105078427 | 11/2015 |
| JP | 2011-224085 | 11/2011 |
| SE | 526576 | 10/2005 |

OTHER PUBLICATIONS

European Search Report dated Jul. 31, 2018 issued in counterpart application No. 16876027.0-1132, 9 pages.
Chinese Office Action dated Apr. 9, 2020 issued in counterpart application No. 201680069563.3, 24 pages.
Chinese Office Action dated Oct. 27, 2020 issued in counterpart application No. 201680069563.3, 29 pages.

* cited by examiner

METHOD AND APPARATUS FOR TRANSMITTING/RECEIVING HEALTH INFORMATION USING HUMAN BODY COMMUNICATION

PRIORITY

This application claims priority under 35 U.S.C. § 119(a) to Korean Patent Application Serial No. 10-2015-0178487, which was filed in the Korean Intellectual Property Office on Dec. 14, 2015, the entire disclosure of which is incorporated herein by reference.

BACKGROUND

1. Field of the Disclosure

The present disclosure relates generally to healthcare technology, and more particularly, to methods and apparatuses for measuring a human body condition in order to transmit and receive health information.

2. Description of the Related Art

In order to meet the demand for wireless data traffic soaring since the 4G communication system came to the market, there are ongoing efforts to develop enhanced 5G communication systems or pre-5G communication systems. For the reasons, the 5G communication system or pre-5G communication system is called the beyond 4G network communication system or post LTE system.

For higher data transmit rates, 5G communication systems are considered to be implemented on ultra-high frequency bands (mm Wave), such as, e.g., 60 GHz. To mitigate pathloss on the ultra-high frequency band and increase the reach of radio waves, the following techniques are taken into account for the 5G communication system: beamforming, massive multi-input multi-output (MIMO), full dimensional MIMO (FD-MIMO), array antenna, analog beamforming, and large scale antenna.

Also being developed are various technologies for the 5G communication system to have an enhanced network, such as evolved or advanced small cell, cloud radio access network (cloud RAN), ultra-dense network, device-to-device (D2D) communication, wireless backhaul, moving network, cooperative communication, coordinated multi-point (CoMP), and interference cancellation.

There are also other various schemes under development for the 5G system including, e.g., hybrid FSK and QAM modulation (FQAM) and sliding window superposition coding (SWSC), which are advanced coding modulation (ACM) schemes, and filter bank multi-carrier (FBMC), non-orthogonal multiple access (NOMA) and sparse code multiple access (SCMA), which are advanced access schemes.

Meanwhile, the Internet is evolving from the human-centered connection network by which humans create and consume information to the Internet of Things (IoT) network by which information is communicated and processed between things or other distributed components. The Internet of Everything (IoE) technology may be an example of a combination of the Big data processing technology and the IoT technology through, e.g., a connection with a cloud server.

To implement the IoT, technology elements, such as a sensing technology, wired/wireless communication and network infra, service interface technology, and a security technology, are required. There is a recent ongoing research for inter-object connection technologies, such as the sensor network, Machine-to-Machine (M2M), or the Machine-Type Communication (MTC).

In the IoT environment may be offered intelligent Internet Technology (IT) services that collect and analyze the data generated by the things connected with one another to create human life a new value. The IoT may have various applications, such as the smart home, smart building, smart city, smart car or connected car, smart grid, health-care, or smart appliance industry, or state-of-art medical services, through conversion or integration of existing IT technologies and various industries.

Thus, there are various ongoing efforts to apply the 5G communication system to the IoT network. For example, the sensor network, machine-to-machine (M2M), machine type communication (MTC), or other 5G techniques are implemented by schemes, such as beamforming, multi-input multi-output (MIMO), and array antenna schemes. The above-mentioned application of the cloud radio access network as a Big data processing technique may be said to be an example of the convergence of the 5G and IoT technologies.

The continued development of communication technology has led to research of technology for data communication between electronic devices contacting a human body, which communicate using the human body as a transmission medium, i.e., human body communication technology. Human body communication may generate an electric current flow or electric field between the electronic devices contacting the human body, providing data communication using the human body as a medium. Human body communication may transmit data at a transmission rate of a few tens of Kbps or Mbps, and various applications using human body communications are currently under development.

Various sensors have been developed for measuring human body conditions, e.g., blood pressure, blood sugar, electrocardiogram (ECG), heart rate, etc. For example, such a sensor for measuring human body conditions may be constructed as a patch that attaches onto the human body. Information regarding the measured human body may be delivered to a medical device or a user's electronic device, which is connected, via wire or wirelessly, with the sensor.

Herein, the information regarding the measured human body is referred as "health information". Health information is material information directly involving the user's health, and thus, a correct measurement of a body condition through sensors is critical. Further, the health information is personal information, requiring safe transmission and reception not to be hacked.

SUMMARY

The present disclosure addresses at least the above-mentioned problems and/or disadvantages and provides at least the advantages described below.

According to an aspect of the present disclosure, a method and apparatus are provided for safely transmitting and receiving health information using human communications.

According to another aspect of the present disclosure, a method and apparatus are provided for safely transmitting and receiving health information and administration information using human communications.

According to another aspect of the present disclosure, a method and apparatus are provided for determining a proper communication scheme depending on the type of information to efficiently transmit and receive health information.

In accordance with an aspect of the present disclosure, a method is provided for transmitting health information by an electronic device. The method includes receiving, from a terminal, a first message requesting the health information;

measuring a body condition, in response the first message; and transmitting, to the terminal, a second message including the health information by using human body communication, the health information being based on the measured body condition.

In accordance with another aspect of the present disclosure, an electronic device is provided transmitting health information. The electronic device includes an electrode unit including multiple electrodes for human body communication with a terminal and measurement of a body condition; and a controller configured to control receiving, from the terminal, a first message requesting the health information, measuring the body condition, in response the first message, and transmitting, to the terminal, a second message including the health information by using the human body communication, the health information being based on the measured body condition.

In accordance with another aspect of the present disclosure, a method is provided for receiving health information by a terminal. The method includes transmitting, to an electronic device using human body communication, a first message requesting the health information; and receiving, from the electronic device, a second message including the health information by using the human body communication, the health information being based on a body condition measured by the electronic device.

In accordance with another aspect of the present disclosure, a terminal is provided receiving health information. The terminal includes an electrode configured to perform human body communication with an electronic device; and a controller configured to control transmitting, to the electronic device using human body communication, a first message requesting the health information, and receiving, from the electronic device, a second message including the health information by using the human body communication, the health information being based on based on a body condition measured by the electronic device.

BRIEF DESCRIPTION OF THE DRAWINGS

The above and other aspects, features, and advantages of certain embodiments of the present disclosure will be more apparent from the following detailed description taken in conjunction with the accompanying drawings, in which.

Throughout the drawings, like reference numerals may refer to like parts, components, and/or structures.

DETAILED DESCRIPTION

Figure 1:
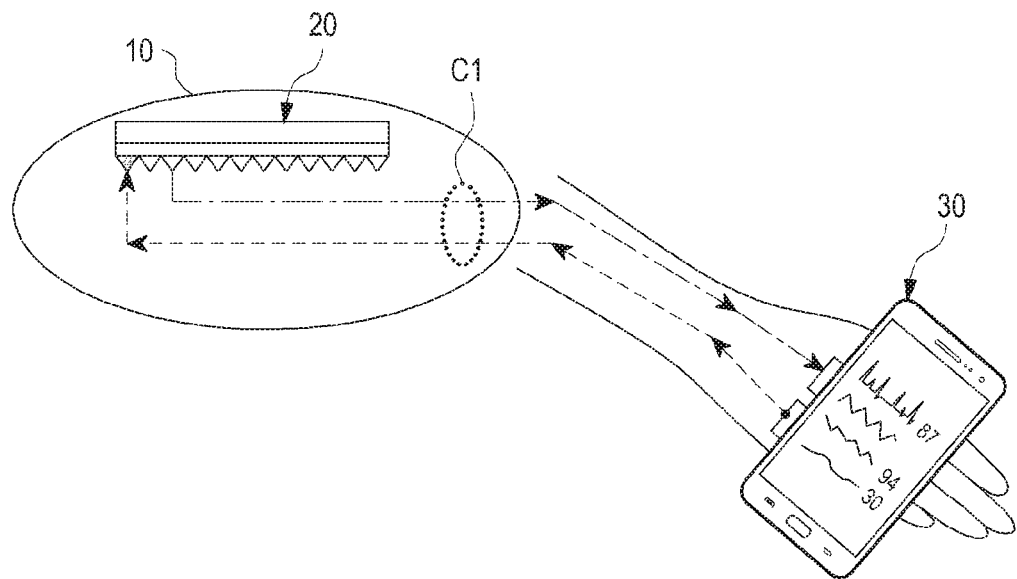
FIG. 1 illustrates a method for transmitting and receiving health information using human body communication according to an embodiment of the present disclosure.

Various embodiments of the present disclosure will be described in detail below with reference to the accompanying drawings.

What is well known in the related art in the following description of the embodiments will be omitted for technical details that are not directly related to the present disclosure, in order to more clearly convey the subject matter of the present disclosure. For the same reason, in the accompanying drawings, some components may be exaggerated, omitted or shown schematically. In addition, the size of each component may not reflect its actual size. The same or corresponding components in the drawings are assigned the same reference numerals.

Herein, the term "human body communication" indicates communication technology for data communication between electronic devices contacting a human body, using the human body as a communication medium.

The term "patch" indicates an electronic device including at least one sensor having an electrode structure attached to a human body to measure a (human) body condition.

The term "terminal" may denote a portable terminal, a fixed terminal, and/or a wearable device, such as a smartphone, a smart watch, a smart bracelet, a tablet personal computer (PC), a phablet, a laptop computer, or a desktop PC, which is equipped with an application for transmitting and receiving health information and administration information based on the health information to/from a patch using the human body communication or wireless communication.

The term "health information" indicates various types of information indicating a user's (human) body condition, such as the user's blood pressure, blood sugar, electrocardiogram (ECG), heart rate, etc., measured using a patch.

The term "administration information" indicates information transmitted from a terminal to adjust, e.g., the amount of a drug injected into a human body through a patch or an administration period based on health information. The administration information may be provided from a server of a business operator providing a healthcare service to a terminal.

Various short-range wireless communication technology may be used by the terminal, such as device-to-device (D2D) communication, Bluetooth communication, Bluetooth low energy (BLE) communication, ZigBee, z-wave, Wi-Fi communication, and/or various cellular communication technology may be used by the terminal, such as long term evolution (LTE) communication or wireless broadband (wibro) communication.

FIG. 1 illustrates a method for transmitting and receiving health information using human body communication according to an embodiment of the present disclosure.

Referring to FIG. 1, a patch 20, which is an electronic device including at least one sensor (or sensor electrode) having an electrode structure for measuring a body condition, is attached to a human body 10. Herein, the terms "sensor" and "sensor electrode" may be interchangeably used, and may be understood as having the same meaning.

The electrode structure may be provided in various types, e.g., an invasive type, which has a needle-shaped electrode, as illustrated in FIG. 1, a wide type, which has a circular or polygonal electrode, which is attached to the human body in a relatively larger area than that of the invasive type, or a hybrid type, which is a combination of the invasive type and the wide type. The electrode structure of the patch 20 may be of an appropriate type selected according to a body condition to be measured, e.g., blood pressure, blood sugar, ECG, heart rate, body fat percentage, brainwave, etc.

A terminal 30 requests the patch 20 to transmit health information using human body communication C1. In response to the request, the patch 20 measures a body condition through the at least one sensor provided therein. The patch 20 then generates health information including the measured body condition and transmits the generated health information to the terminal 30 using the human body communication C1. A first message through which the terminal 30 sends the request for the health information to the patch 20 and a second message, as a response to the first message, through which the patch 20 transmits the health information to the terminal 30, may include unique identification information so that the terminal 30 may identify whether the received health information corresponds to the requested health information.

For the human body communication C1, at least one side of the terminal 30 includes an input and output electrode for communication through an electrical contact with the human body 10. For example, when the terminal 30 is a smartphone, an input and output electrode for the human body communication C1 may be formed on an edge of the smartphone. When the terminal 30 is a smart watch, an input and output electrode for the human body communication C1 may be formed on the bezel, on the bottom, or on the crown of the watch.

The measurement of the health information may be distinctively or separately performed depending on operation modes, such as an exercise mode, a diet mode, an emotion managing mode, a treatment mode, and a management mode. In the exercise mode, a measurement related to exercise, such as a heart rate measurement, may be performed. In the diet mode, measurement related to weight management, such as of a body fat percentage measurement, may be performed. In the emotion managing mode, measurement related to the human emotion, such as of a heart rate or brainwave measurement, may be performed. In the treatment mode, measurement related to diagnosis of the user's disease or treatment may be performed. In the management mode, whether measurement is normally performed may be determined or a statistical analysis of gathered measurement data may be performed.

Although FIG. 1 illustrates the measurement of health information being performed by one patch, such measurement may also be performed using multiple patches. In this case, the multiple patches may be distinguished for each of the body portions to which the patches, respectively, are attached or based on body conditions (e.g., blood pressure, blood sugar, or heart rate), and each patch may be differentiated and identified by identification information assigned thereto.

Figure 2:
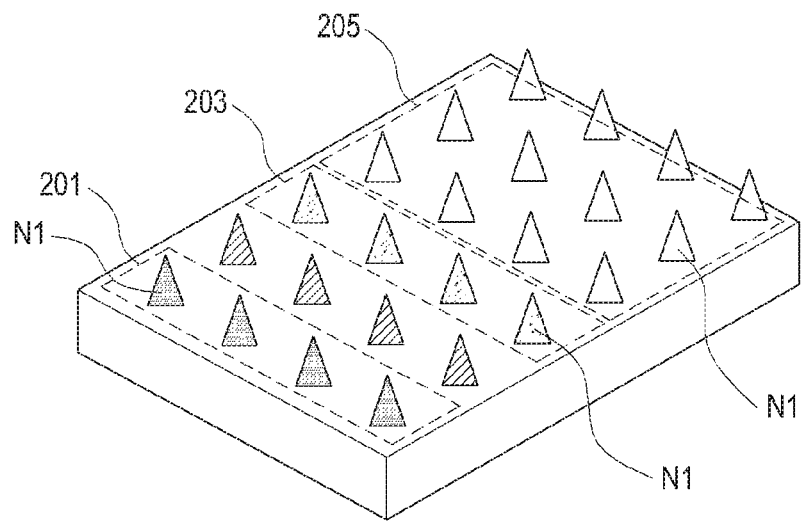
FIG. 2 illustrates an electrode structure of a patch according to an embodiment of the present disclosure.

FIG. 2 illustrates an electrode structure of a patch according to an embodiment of the present disclosure.

Referring to FIG. 2, a patch includes a receiver 201, a transmitter 203, and a sensor unit 205. The receiver 201, the transmitter 203, and the sensor unit 205 each include electrodes N1. Although FIG. 2 illustrates the electrodes N1 as being of an invasive type, the present disclosure is not limited thereto. For example, the electrodes N1 may be an invasive type, wider type, or hybrid type, as described above.

At least one electrode included in the transmitter 203, at least one electrode included in the receiver 201, and at least one electrode included in the sensor unit 205 are referred to as a transmission electrode, reception electrode, and sensor electrode, respectively.

The number of transmission electrodes or reception electrodes used for communication may be adjusted depending on the transmit/receive sensitivity of the human body communication, and the number of sensor electrodes used may also be adjusted depending on the measurement sensitivity. Such adjustment of the number of the electrodes may be performed by a physical manipulation or an electrical control. When the number of the electrodes is adjusted by the electrical control, a command for the adjustment may be transmitted from the terminal to the patch.

When a patch supports measurement of multiple items, such as blood sugar, blood pressure, or heart rate, multiple sensor electrodes of the sensor unit 205 may be arranged on areas differentiated as per the type of the measurement. In this case, upon measuring blood sugar, the sensor electrode of the area for measuring a blood sugar may be activated, without activating other sensor electrodes, and upon measuring other items, only the sensor electrodes for the areas for measuring the items may be activated. When multiple items are simultaneously measured, the sensor electrodes of multiple areas may be activated at the same time.

When the sensor electrode supports measurement of multiple items, a command for differentiating the type of measurement from another may be transmitted from the terminal to the patch, and the patch may control the sensor electrode so that measurement corresponding to the command is performed.

Figure 3A:
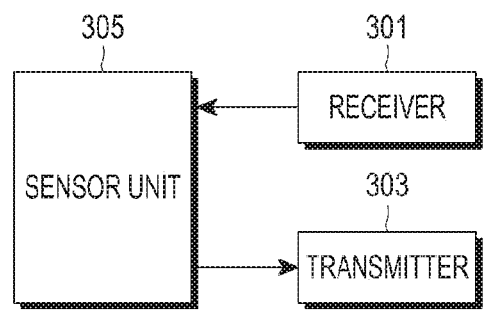
FIG. 3A illustrates a patch according to an embodiment of the present disclosure.

FIG. 3A illustrates a patch according to an embodiment of the present disclosure.

Referring to FIG. 3A, a patch includes a receiver 301, a transmitter 303, and a sensor unit 305.

A first message from a terminal, e.g., a measurement request message, may be received by the patch through at least one reception electrode of the receiver 301. The sensor unit 305, upon receiving the first message, measures a body condition through at least one sensor electrode, gathers measurement results, and transfers health information based on the gathered measurement results to the transmitter 303. A second message, e.g., a measurement response message, includes the health information and may be transmitted to the terminal through at least one transmission electrode of the transmitter 303.

The sensor unit 305 may include a microprocessor for controlling a measurement operation using the sensor electrode and for controlling the transmission and reception operation of the receiver 301 and the transmitter 303. The microprocessor may be included in the sensor unit 305 or as a separate component in the patch.

Figure 3B:
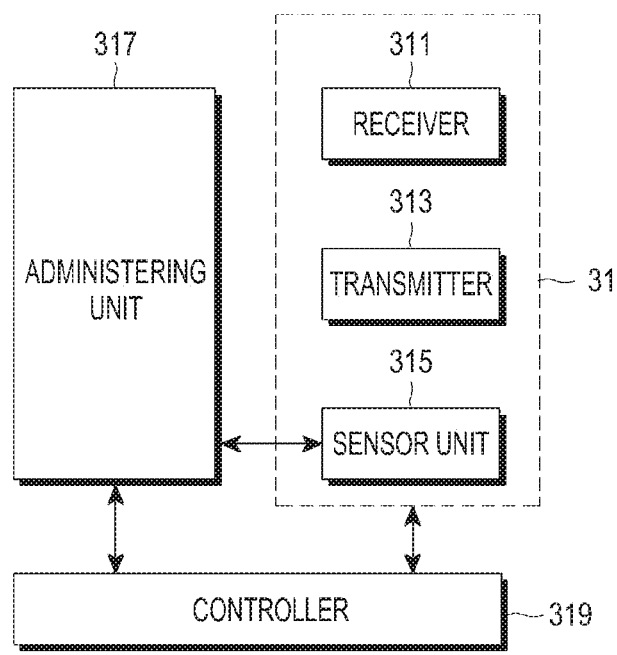
FIG. 3B illustrates a patch according to an embodiment of the present disclosure.

FIG. 3B illustrates a patch according to an embodiment of the present disclosure.

Referring to FIG. 3B, different than the patch of FIG. 3A, the patch illustrated in FIG. 3B includes an administering unit 317 and a microprocessor controller 319 for controlling the overall operation of the patch. In FIG. 3B, reference numeral 31 denotes an electrode unit including a receiver 311, a transmitter 313, and a sensor unit 315. The operations of transmitting and receiving first and second messages by the receiver 311 and the transmitter 313 and the operations of measuring a body condition through at least one sensor electrode and gathering measurement results by the sensor unit 315 are basically the same as those of the receiver 301, transmitter 303, and sensor unit 305 of FIG. 3A. Accordingly, a repetitive description of these elements has been omitted.

The controller 319, however, controls the overall operation of the electrode unit 31, and upon receiving administration information through the receiver 311, the controller 319 controls the administering unit 317 to adjust a variable of the patch, e.g., an amount of a drug injected into the body or an administration period, based on the administration information. The administering unit 317 may provide a drug to be injected into the body to the sensor unit 315 under the control of the controller 319. The drug injected into the body may be stored in the administering unit 317 and delivered from the administering unit 317 to the sensor unit 315.

Alternatively, the drug injected into the body may be stored in at least one sensor electrode of the sensor unit 315. In this case, the sensor electrode may have a cavity therein, in which the drug may be stored, and the sensor unit 315 injects the drug into the human body under the control of the controller 319. Accordingly, the administering unit 317 may selectively be included in the patch.

Figure 4:
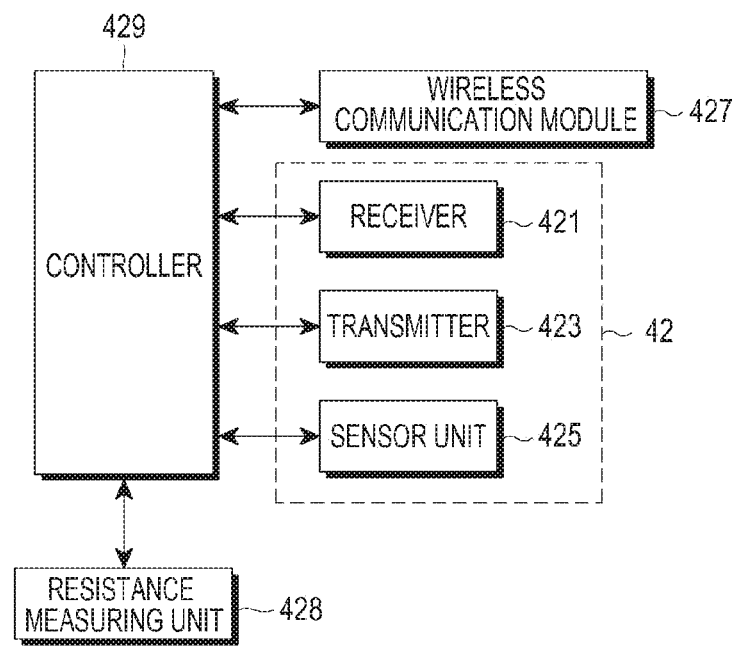
FIG. 4 illustrates a patch according to an embodiment of the present disclosure.

FIG. 4 illustrates a patch according to an embodiment of the present disclosure.

Referring to FIG. 4, different than the patch illustrated FIG. 3A, the patch illustrated in FIG. 4 includes a wireless communication module 427, a resistance measuring unit 428, and a microprocessor controller 429 for controlling the overall operation of the patch. The wireless communication module 427 includes at least one of a communication interface supporting at least one short-range wireless communication scheme and a communication interface supporting at least one cellular communication scheme. Alternatively, the patch may alternatively or additionally include a communication interface supporting wired communications.

In FIG. 4, reference numeral 42 denotes an electrode unit including a receiver 421, a transmitter 423, and a sensor unit 425. The operations of measuring a body condition by the sensor unit 425 and transmitting health information by the receiver 421 and the transmitter 423 are basically the same as those of the receiver 401, the transmitter 403, and the sensor unit 405 described above in connection with FIG. 3A. Accordingly, a repetitive description of these elements has been omitted.

The resistance measuring unit 428 measures a resistance for determining whether each electrode in the electrode unit 42 is in contact with the body for human body communication and transfers the resistance to the controller 429. When the resistance measured through the resistance measuring unit 428 deviates from a predetermined threshold, the controller 429 may notify the terminal that there is a contact failure between the electrode unit 42 and the human body.

Further, the patch may include a separate display device (e.g., a light emitting diode (LED) or display panel), and the contact failure may be notified through the display device.

The resistance measuring unit 428 may selectively be included in the patch. Likewise, the configuration of the patches of FIGS. 3A and 3B may also include a resistance measuring unit and a wireless communication module.

A communication scheme for information to be transmitted or received through the terminal may be determined to be wireless/wired communication depending on the type of the information. For example, transmission and reception of control information for communication access between the patch and the terminal may be performed using wireless communication, e.g., the wireless communication module 427, and transmission and reception of information requiring security, such as health information and administration information, may be performed through human body communication.

During an emergency where human body communication is difficult to perform or for remote treatment, the patch may be controlled through the wireless communication module 427 in a remote site or with the terminal not contacting the human body. Further, the controller 429 may receive a request from the terminal or a request from a remote site (e.g., an external server or external terminal) and control the transmission and reception of health information and/or administration information in a communication scheme indicated by the request.

The patch configurations of FIGS. 2 to 4 may also include a storage unit, e.g., a memory, for storing health information and/or administration information. The patch may periodically measure health conditions, store measurement results in the storage unit, and when the patch and the terminal connect together through human body communication or wireless communication, the patch may send health information including the stored measurement results to the terminal (or an external server). Similarly, an administration report based on administration information may be stored in the storage unit, and when the patch and the terminal establish a communication connection, the administration report may be sent to the terminal (or the external server).

Figure 5:
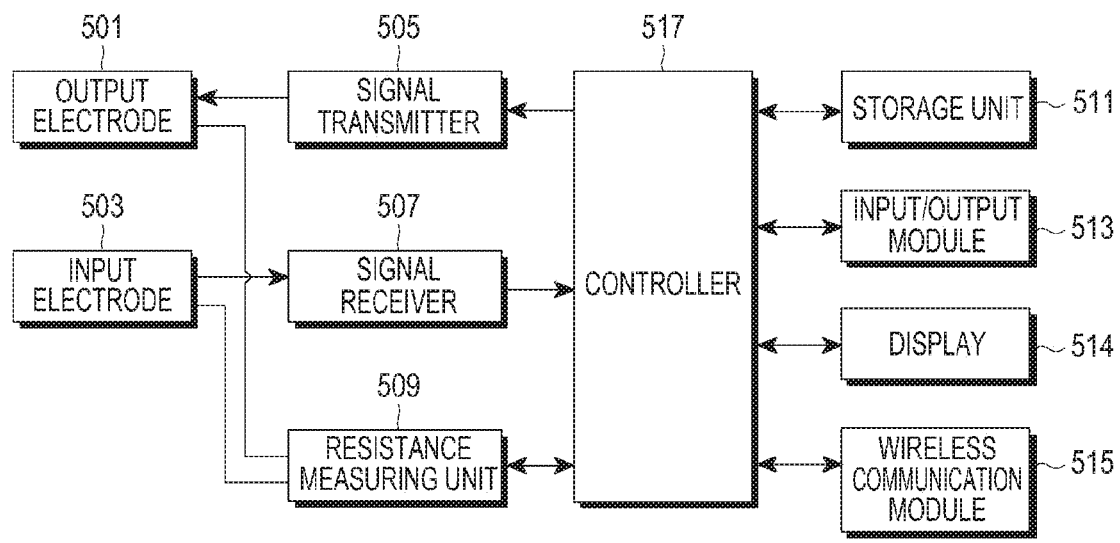
FIG. 5 illustrates a terminal according to an embodiment of the present disclosure.

FIG. 5 illustrates a terminal according to an embodiment of the present disclosure.

Referring to FIG. 5, the terminal includes an output electrode 501, an input electrode 503, a signal transmitter 505, a signal receiver 507, a resistance measuring unit 509, a storage unit 511, an input/output module 513, a display 514, a wireless communication module 515, and a controller 517.

The output electrode 501 and the input electrode 503 are electrodes contacting the human body for human body communication. Although the output electrode 501 and the input electrode 503 are separately illustrated, they may also be configured in a single electrode.

A first message, e.g., a measurement request message, is transmitted to a patch through the output electrode 501, and the second message, e.g., a measurement response message, is received from the patch through the input electrode 503.

The resistance measuring unit 509 measures a resistance for determining whether the output electrode 501 and the input electrode 503 are in contact with the human body and transfers the resistance to the controller 517. When the resistance measured through the resistance measuring unit 509 deviates from a predetermined threshold, the controller 517 may notify the user, through the display 514, that there is a contact failure between the human body and at least one of the output electrode 501 and the input electrode 503. The resistance measuring unit 509 is an optional component and may thus be omitted.

The signal transmitter 505 and the signal receiver 507 are communication interfaces for transmitting and receiving health information and/or administration information to/from the patch through human body communication.

The storage unit 511 stores an operating system (OS) for basic operation of the terminal, and various applications, such as an application for transmitting and receiving health information and/or administration information to/from the patch using human body communication or wireless/wired communication. The storage unit 511 may also store the health information and administration information.

The input/output module 513 may include buttons for performing various functions, a microphone, a speaker, a vibration motor, a connector, and/or a keypad.

The connector may include a communication interface for wired communication with the patch.

The display 514 may display an operation screen of the terminal and may include a touch panel that provides a touch user interface for the operation of the terminal.

The wireless communication module 515 may include a communication interface supporting a short-range wireless communication scheme and/or a communication interface supporting a cellular communication scheme.

The controller 517 controls the overall operation of the terminal, e.g., controls a soft key displayed on the touch panel to be selected in response to a user's gesture sensed on the touch panel or runs a corresponding application or relevant function. The user's gesture may include a touch by a finger or tool or motion recognition by the human body.

The controller 517 controls the operations of determining whether there is a contact to the human body for human body communication through the output electrode 501, input electrode 503, and resistance measuring unit 509, sending a request for health information to the patch according to a user's key entry or a remote command from an external server (or an external terminal), and receiving health information from the patch. The controller 517 also controls operations of analyzing the health information received from the patch and displaying information through the display 514.

Further, the controller 517 controls operations of transmitting the health information to the external server (or external terminal) and transmitting administration information received from the external server (or external terminal) to the patch.

The controller 517, upon receiving health information, may control the operation of transmitting the administration information based on the health information to the patch according to an operation of the application.

Figure 6:
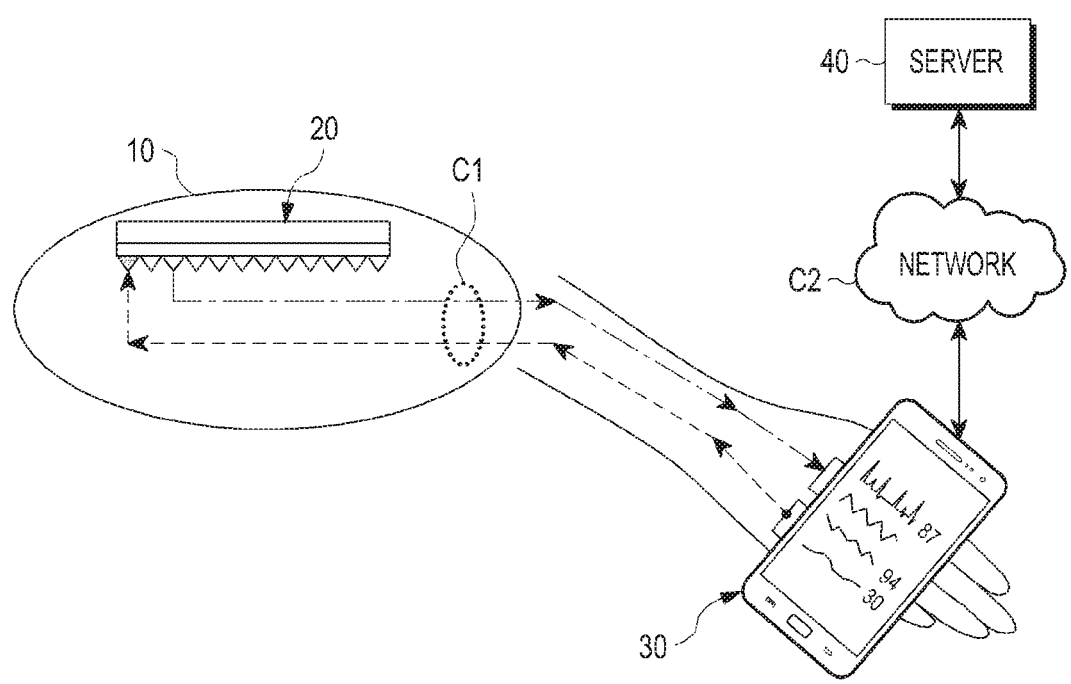
FIG. 6 illustrates a method for transmitting and receiving health information using human body communication according to an embodiment of the present disclosure.

FIG. 6 illustrates a method for transmitting and receiving health information using human body communication according to an embodiment of the present disclosure.

Referring to FIG. 6, the operations of transmitting and receiving health information and administration information between the patch 20 and the terminal 30 using human body communication C1 are the same as those illustrated in in FIG. 1. However, in FIG. 6, the terminal 30 and an external server 40 (or an external terminal) may also transmit and receive health information and administration information through a network C2, e.g., the Internet. For example, the terminal 30 sends health information received through the patch 20 to the external server 40, and the external server 40 sends, in response, administration information based on the health information to the terminal 30. The terminal 30 then sends the administration information received from the external server 40 (or external terminal) to the patch 20. The method in FIG. 6 allows for remote administration using the patch 20 through the external server 40 (or external terminal) available, e.g., to a medical doctor.

In the above-described embodiments, the health information and administration information may be transmitted or received as encrypted information. The encryption/decryption of the health information and administration information may be performed using at least one combination of various pieces of health information, e.g., the user's unique information, such as ECG, fingerprint information, iris information, etc.

Figure 7:
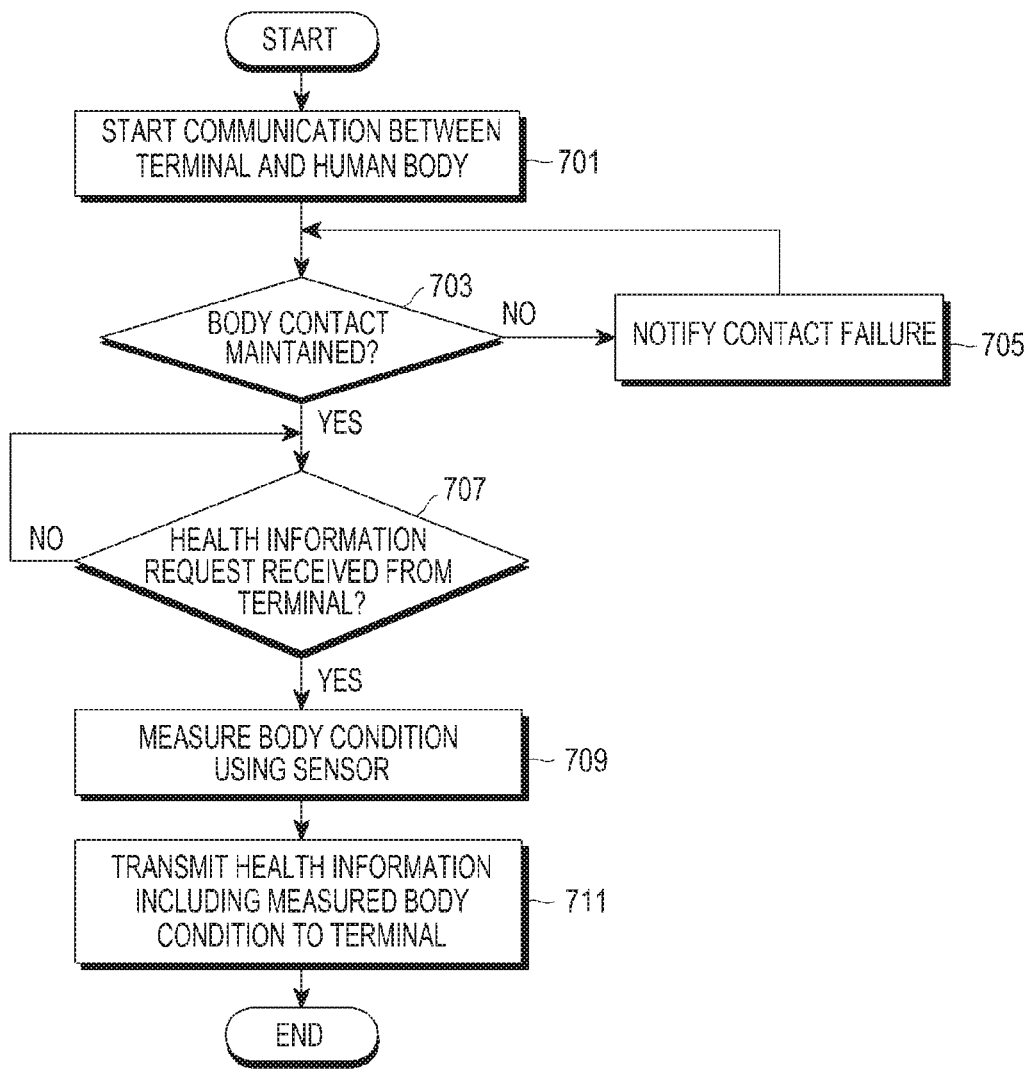
FIG. 7 is a flowchart illustrating a method of transmitting health information, by a patch, using human body communication according to an embodiment of the present disclosure.

FIG. 7 is a flowchart illustrating a method of transmitting health information, by a patch, using human body communication according to an embodiment of the present disclosure.

Referring to FIG. 7, when a patch is attached onto a user's body, and an application for transmission and reception of health information is driven with the user holding the terminal in step 701, the patch starts human body communication with the terminal.

In step 703, the patch determines whether a contact to the human body through an electrode is maintained, e.g., by comparing a resistance measured through the electrode of the patch with a predetermined threshold. When it is determined that the measured resistance deviates from the threshold, the patch determines that a contact failure exists in step 703, and notifies the user that the patch is subjected to a contact failure in step 705. The notification of the contact failure may be performed through an LED indicating an operation state of the patch or wireless communication with the terminal.

Thereafter, if the user adjusts the state of attachment of the patch, the patch determines whether a contact to the human body through an electrode is maintained again in step 703.

While contact is maintained, the patch determines if a first message for requesting health information is received from the terminal in step 707. For example, the first message may indicate an operation mode related to a type of measurement to be performed and a body condition to be measured.

When the patch receives the first message from the terminal in step 707, the patch measures a body condition using a sensor (e.g., the sensor unit 215 of FIG. 2) in step 709. The measurement may be performed as per the operation mode or the body condition to be measured, as indicated in the first message.

In step 711, the patch sends, to the terminal, a second message including health information based on the measured body condition.

Step 709 may selectively be modified or omitted according to the type of the request for health information received in step 707. For example, when the health information request received in step 707 is a measurement request, the measurement may be performed in step 709 and transmitted in step 711, as illustrated. However, when the health information request received in step 707 is a transmission request, step 711 may be performed, without performing step 709. For example, the measurement may have been performed before receiving the health information request in step 707 and the health information based on the measurement may have been previously stored. Accordingly, the patch may send the second message including health information related to the measured body condition to the terminal in step 711, without performing step 709.

Figure 8:
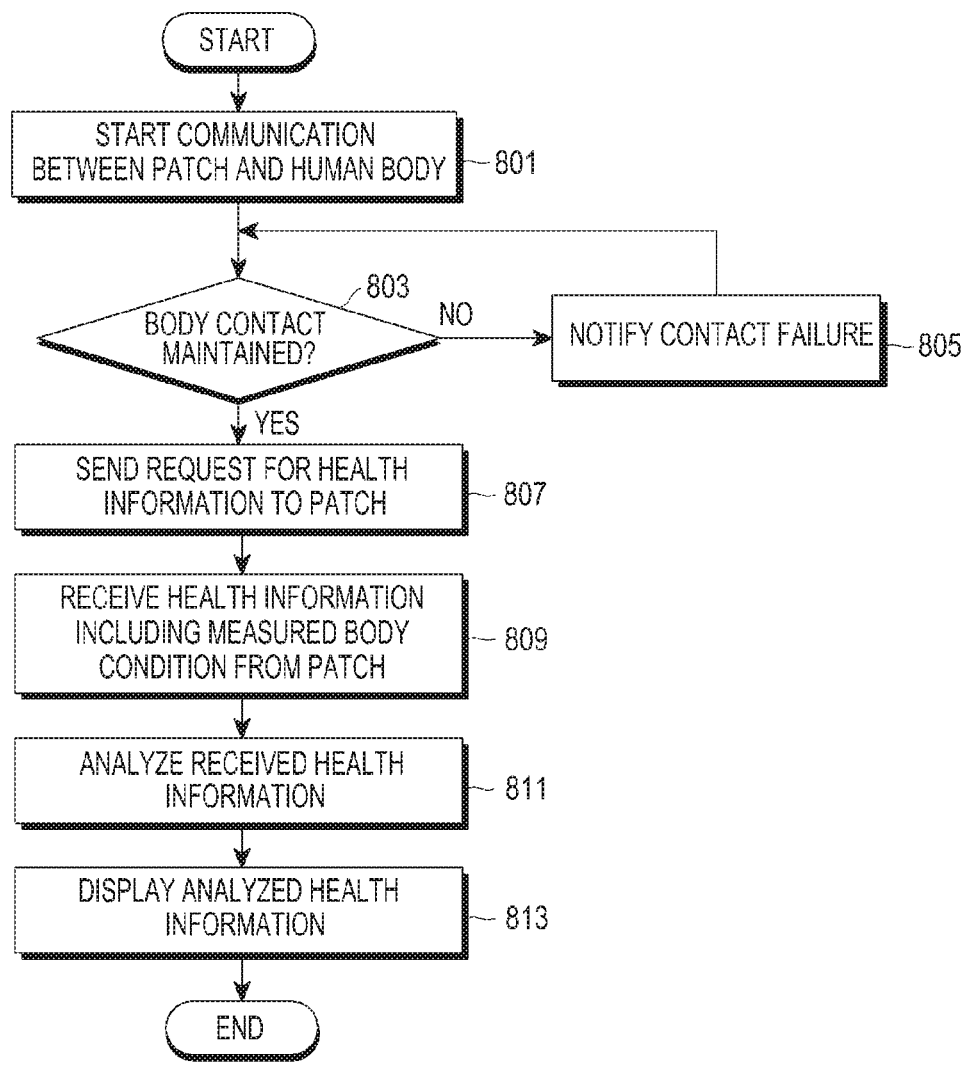
FIG. 8 is a flowchart illustrating a method of receiving health information, by a terminal, using human body communication according to an embodiment of the present disclosure.

FIG. 8 is a flowchart illustrating a method of receiving health information, by a terminal, using human body communication according to an embodiment of the present disclosure. Specifically, FIG. 8 illustrates a receiving method corresponding to the transmitting method illustrated in FIG. 7.

Referring to FIG. 8, when a patch is attached onto a user's body, and an application for transmission and reception of health information is driven with the user holding the terminal in step 801, the terminal starts human body communication with the patch.

In step 803, the terminal determines whether a contact to the human body through an input and output electrode is maintained, e.g., by comparing a resistance measured through the electrode of the terminal with a predetermined threshold. When it is determined that the measured resistance deviates from the threshold, the terminal determines that a contact failure exists in step 803, and notifies the user that the contact failure exists in step 805. For example, the notification of the contact failure may be performed through the display of the terminal.

If the user adjusts the state of holding the terminal so that the terminal contacts the human body, the terminal may determine whether a contact to the human body through the input and output electrode is maintained again in step 803.

While the contact is maintained and a request for measuring a body condition is received, e.g., is input by a user's key manipulation using an application, the terminal sends a first message for requesting health information to the patch using human body communication in step 807. For example, the first message may indicate an operation mode related to a measurement to be performed and/or a body condition to be measured.

When the measurement by the patch is then complete, the terminal receives a second message including health information based on the measured body condition from the patch in step 809.

In step 811, the terminal analyzes the received health information using the application, and in step 813, the terminal displays the analyzed health information in order for the user to identify the measured body condition through the displayed health information.

Figure 9:
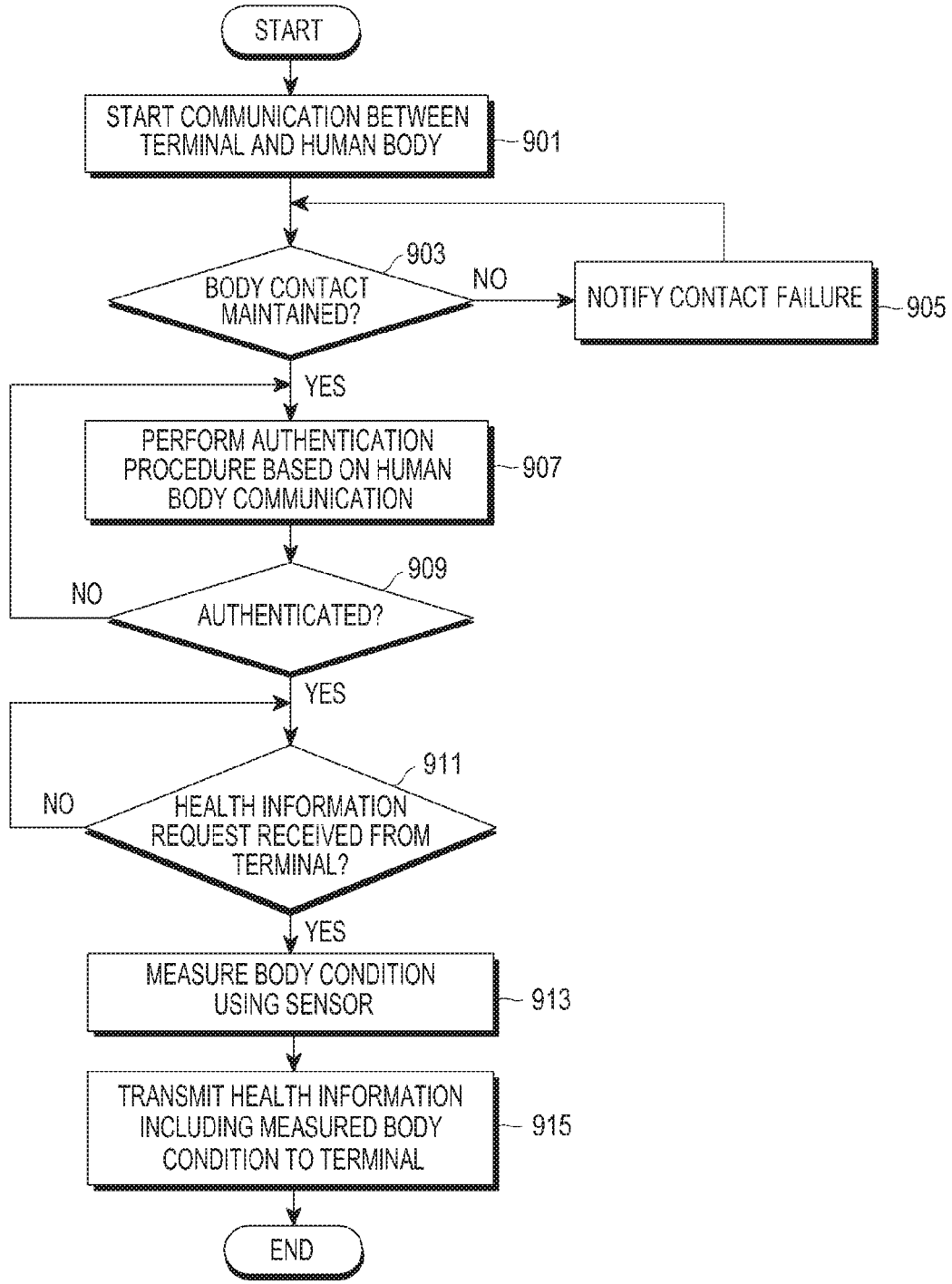
FIG. 9 is a flowchart illustrating a method of transmitting health information, by a patch, using human body communication according to an embodiment of the present disclosure.

FIG. 9 is a flowchart illustrating a method of transmitting health information, by a patch, using human body communication according to an embodiment of the present disclosure. Specifically, the method of FIG. 9 is similar to that of FIG. 7, except that FIG. 9 adds a human body communication-based authentication operation in steps 907 and 909. Accordingly, steps 901 to 905 and 911 to 915, which are related to authentication, are the same as steps 801 to 813 of FIG. 7, and a repetitive description thereof is omitted below.

The human body communication-based authentication operations of steps 907 and 909 are for verifying whether the user using human body communication is a valid one. Because health information is personal, material information, these steps may be performed for security purposes.

Referring to FIG. 9, while contact is maintained between the patch and the body, an authentication procedure is performed in step 907. Authentication may be performed using a piece of information that uniquely identifies the user, such as the user's ECG information or fingerprint information. For example, when the ECG information is used, the patch receives a request for ECG information of the health information from the terminal, e.g., according to the method illustrated in FIG. 7. The terminal is assumed to have the user's ECG information previously registered. The terminal compares the ECG information measured from the patch with the ECG information previously registered in the terminal, and when they match (e.g., when a comparison of the ECG information measured from the patch and the ECG information previously registered in the terminal meet a predetermined tolerance range), the terminal authenticates the user as a valid one and sends an authentication message for the user to the patch.

In step 909, the patch, upon reception of the authentication message, performs steps 911 to 915 of the method. Since others are stopped from measuring a body condition using the user's terminal by the authentication operation, unauthorized use can be prevented.

Figure 10:
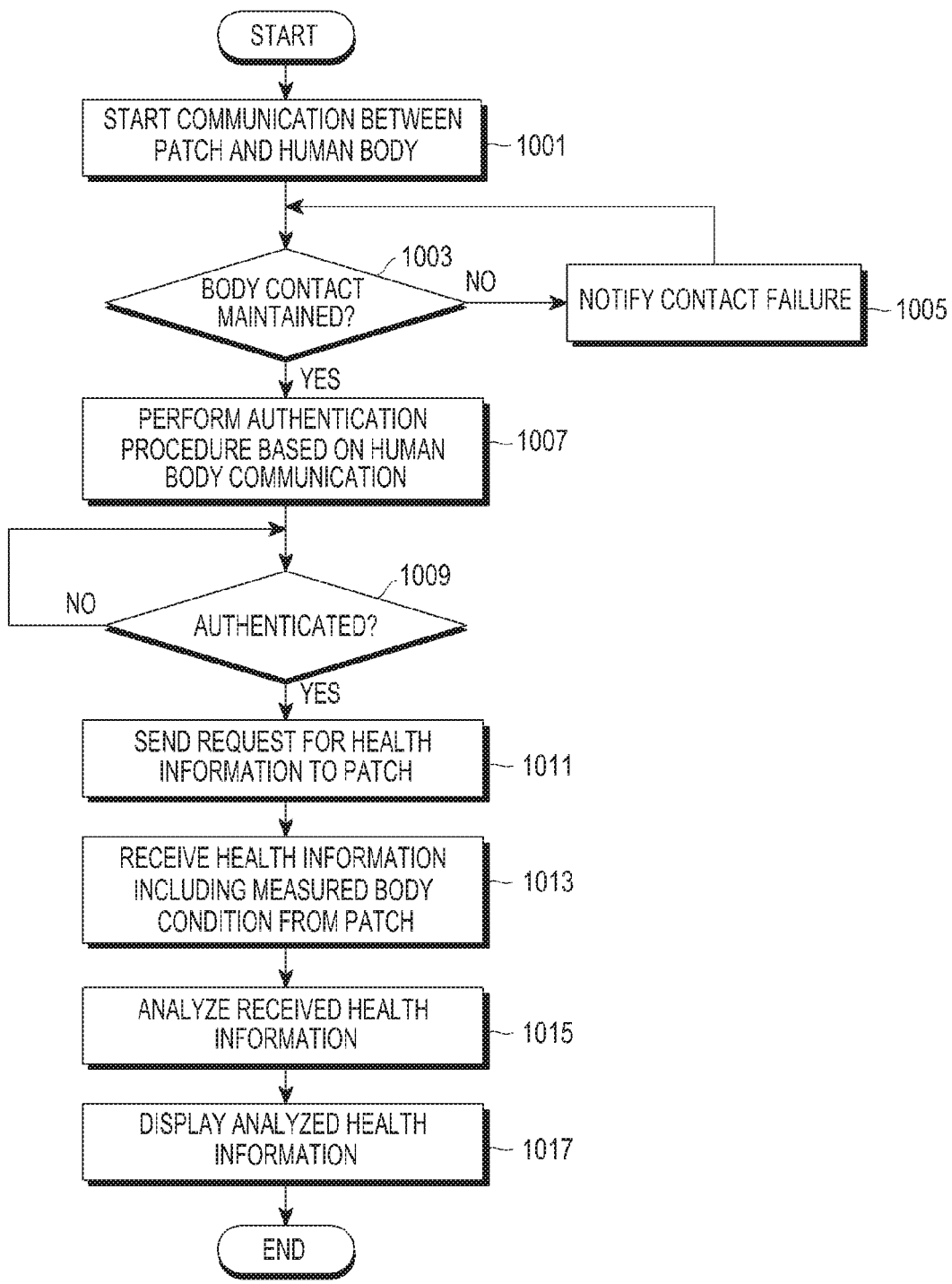
FIG. 10 is a flowchart illustrating a method of receiving health information, by a terminal, using human body communication according to an embodiment of the present disclosure.

FIG. 10 is a flowchart illustrating a method of receiving health information, by a terminal, using human body communication according to an embodiment of the present disclosure. Specifically, FIG. 10 illustrates a receiving method corresponding to the transmitting method illustrated in FIG. 9.

Further, the method of FIG. 10 is similar to that of FIG. 8, except that FIG. 10 adds a human body communication-based authentication operation in steps 1007 and 1009. Accordingly, steps 1001 to 1005 and 1011 to 1017, which are related to authentication are the same as steps 801 to 813 of FIG. 8, and a repetitive description thereof is omitted below.

As described above, the human body communication-based authentication operations in steps 1007 and 1009 are for verifying whether the user using human body communication is a valid one. Here, the terminal is assumed to have the user's ECG information previously registered.

Referring to FIG. 10, while contact is maintained between the terminal and the body, the terminal compares the ECG information measured from the patch with the ECG information previously registered in the terminal, and when they match (e.g., when a comparison of the ECG information measured from the patch and the ECG information previously registered in the terminal meets a predetermined tolerance range) in step 1007, the terminal authenticates the user as a valid, and sends an authentication message to the patch in step 1009.

Thereafter, the terminal performs steps 1011 to 1017 of the method.

When the user is not authenticated in step 1009, after the authentication in step 1007 is repeated a predetermined number of times, the terminal may determine that the user is an invalid user and put a security lock on the terminal to prevent additional authentication attempts.

Figure 11:
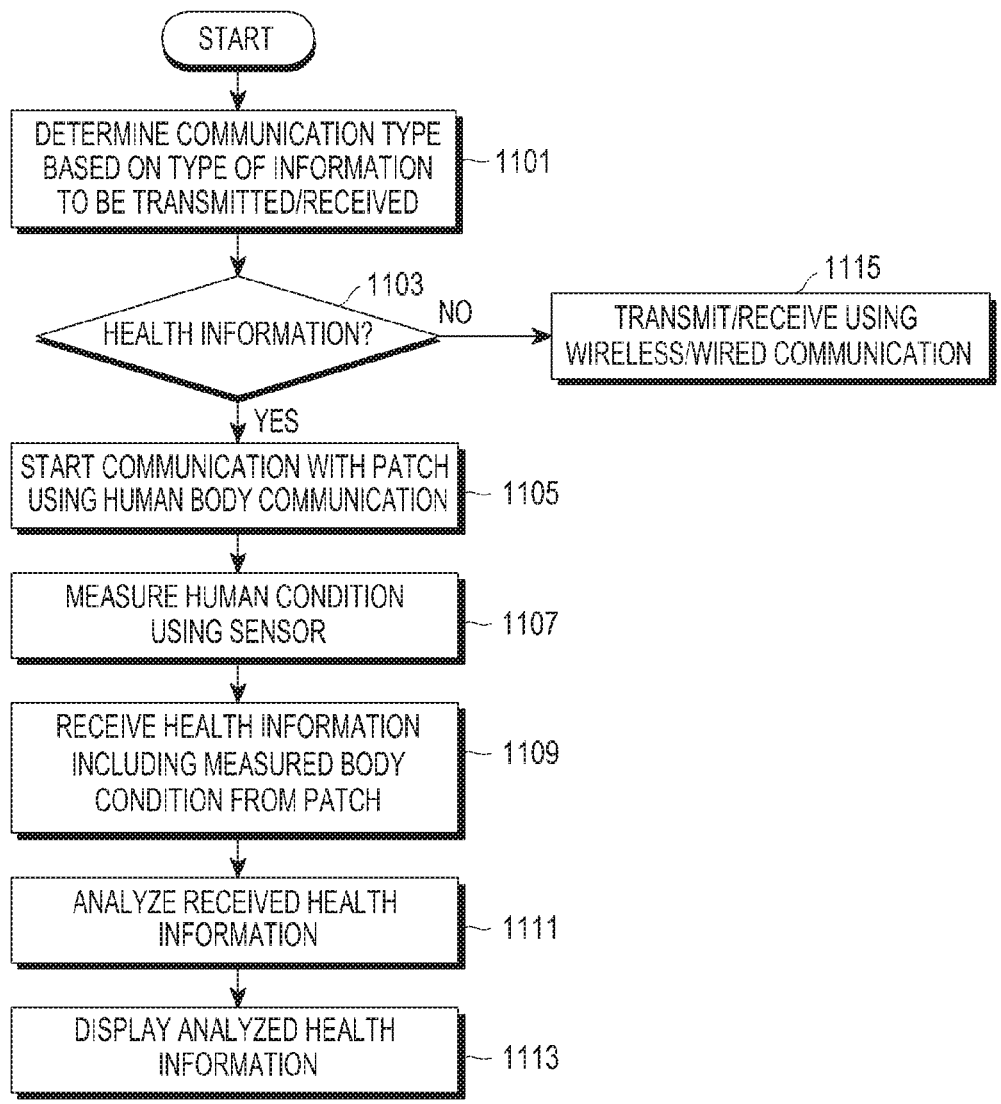
FIG. 11 is a flowchart illustrating a method of receiving health information, by a terminal, using human body communication according to an embodiment of the present disclosure.

FIG. 11 is a flowchart illustrating a method of receiving health information, by a terminal, using human body communication according to an embodiment of the present disclosure. Specifically, the method of FIG. 11 is similar to that of FIG. 8, except that in FIG. 11 the terminal determines a communication scheme based on the type of information to be transmitted and received. Although not illustrated in FIG. 11, determining whether there is a contact to the human body based on a resistance may optionally be performed. Steps 1105 to 1113 of FIG. 11, in which the terminal sends a request for health information to the patch using human body communication, receives the health information, analyzes the received health information, and displays the analyzed health information are the same as steps 801 and 807 to 813 of FIG. 8, and therefore, a repetitive description thereof is omitted below.

Referring to FIG. 11, the terminal determines whether a communication scheme for transmitting and receiving information, is human body communication or wireless/wired communication, based on the type of the information, in steps 1101 and 1103. When the information to be transmitted or received is health information requiring security in steps 1101 and 1103, the terminal determines that the communication scheme is human body communication and starts communication the path using the human body communication in step 1105. However, when the information to be transmitted or received is control information requiring relatively less security than health information in steps 1101 and 1103, the terminal transmits and receives the control information using wireless/wired communication in step 1115. The control information may contain various pieces of control information for transmitting and receiving the health information.

Thus, according to the method of FIG. 11, the amount of data transmitted and received through human body communication may be reduced, enabling more stable transmission and reception of health information and administration information.

Figure 12:
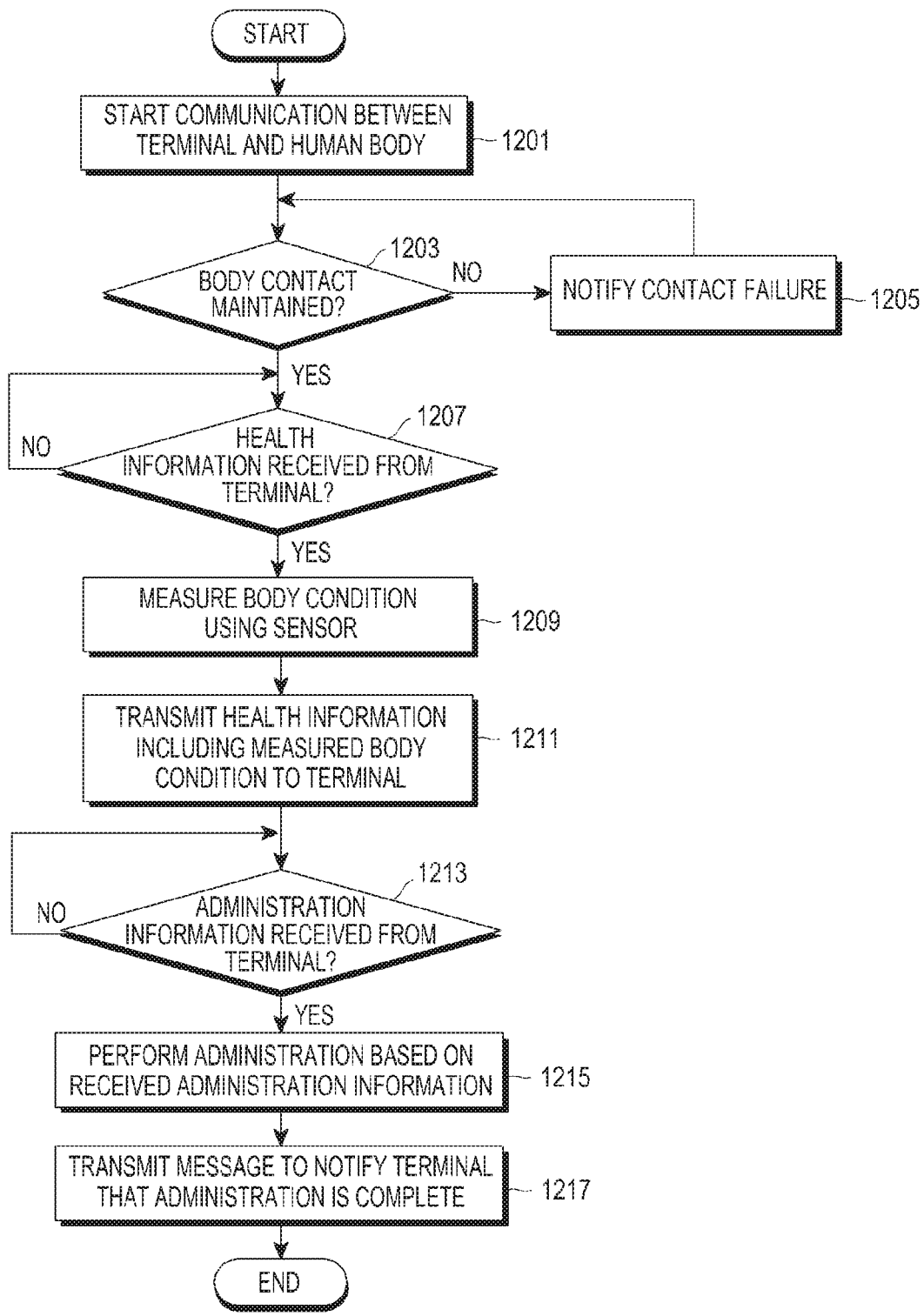
FIG. 12 is a flowchart illustrating a method of receiving health information, by a patch, using human body communication according to an embodiment of the present disclosure.

FIG. 12 is a flowchart illustrating a method of receiving health information, by a patch, using human body communication according to an embodiment of the present disclosure. Specifically, the method of FIG. 12 is similar to that of FIG. 7, except that the method of FIG. 12 includes the patch receiving administration information based on health information from the terminal and performing administration. Accordingly, steps 1201 to 1211 of FIG. 12 are the same as steps 701 to 711 of FIG. 7, and therefore, a repetitive description thereof is omitted below.

Referring to FIG. 12, the patch sends health information to the terminal in steps 1201 to 1211 and waits to receive administration information, which is based on the health information, from the terminal, in step 1213.

Upon receiving the administration information in step 1213, the patch performs administration, e.g., to inject a drug into the human body based on the received administration information, in step 1215. When the administration is complete, the patch transmits a message indicating that the administration is complete to the terminal in step 1217.

Figure 13:
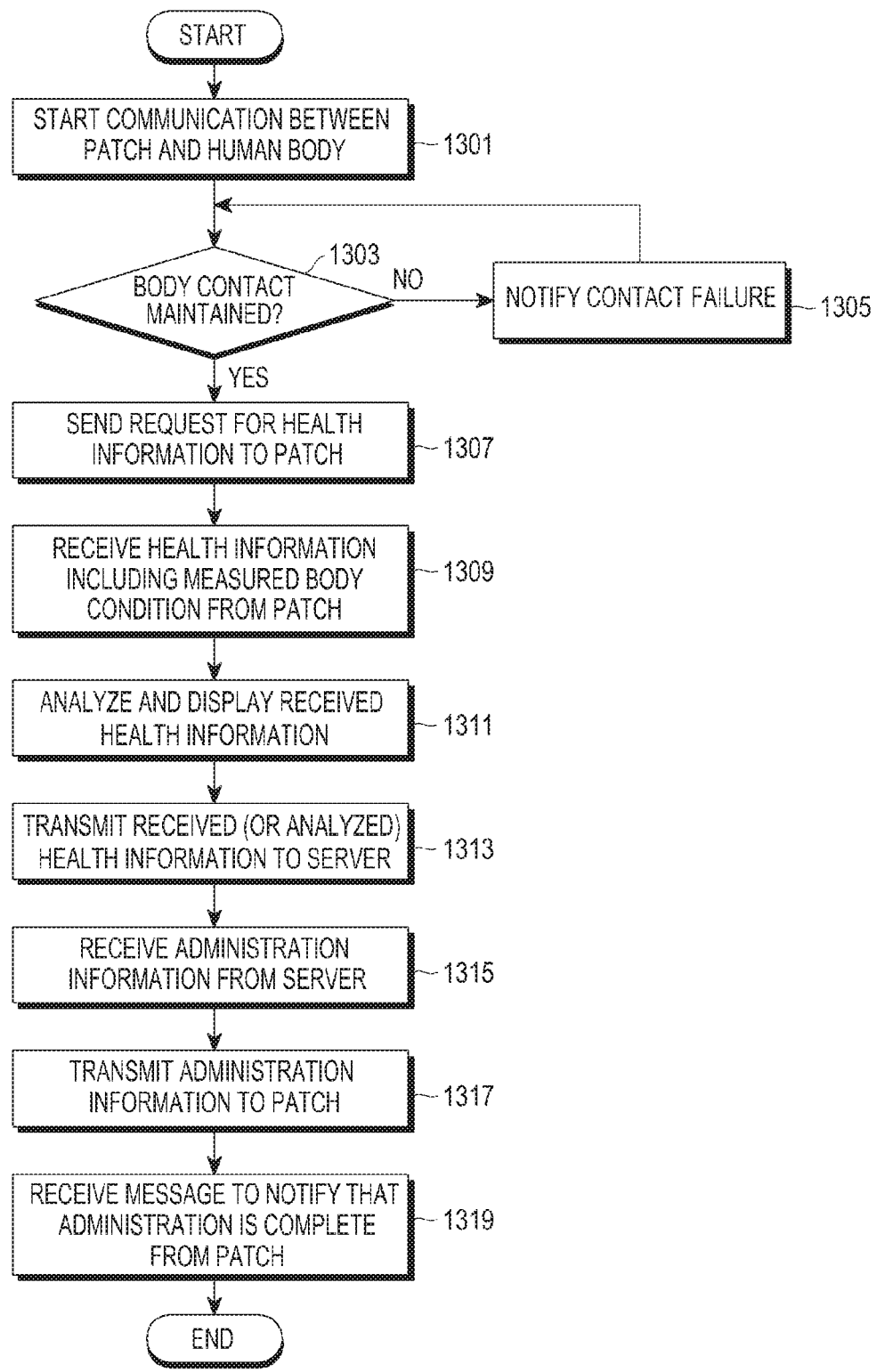
FIG. 13 is a flowchart illustrating a method of receiving health information, by a terminal, using human body communication according to an embodiment of the present disclosure.

FIG. 13 is a flowchart illustrating a method of receiving health information, by a terminal, using human body communication according to an embodiment of the present disclosure. Specifically, the method of FIG. 13 is similar to that of FIG. 8, except that that the method of FIG. 13 includes the terminal receiving health information and sending administration information to the patch based on the received health information. Accordingly, steps 1301 to 1311 of FIG. 13 are the same as steps 801 to 811 of FIG. 8, and therefore, a repetitive description thereof is omitted below.

Referring to FIG. 13, the terminal receives the health information from the patch in steps 1301 to 1311 and sends the received (or analyzed) health information to a server, e.g., as described above in connection with reference to FIG. 6, in step 1313.

In step 1315, the terminal receives administration information based on the health information from the server.

In step 1317, the terminal sends the administration information to the patch. Alternatively, the terminal may directly, rather than receiving the administration information from the server, send the administration information based on the health information to the patch according to an application in the terminal. In this case, the application may previously store and use table information mapped with administration information corresponding to various measurement results indicating body conditions.

After the administration is complete, the terminal receives a message indicating that the administration is complete from the patch in step 1319.

According to the above-described embodiments of the present disclosure, health information may be safely transmitted and received using human body communication, and a user may be promptly provided with a medical service and/or remote treatment using the administration information based on the health information. Further, a communication scheme may be determined depending on the type of information to be transmitted or received. Thus, the amount of data transmitted and received through human body communication may be reduced, enabling more stable transmission and reception of health information and administration information.

Although the above-described embodiments of the present disclosure are directed to human body communication, the present disclosure is also applicable to animal body communication. For example, a terminal can be place into contact with an animal wearing a patch, and the terminal and the patch can communicate through animal body communication according to the above-described embodiments.

While the disclosure has been shown and described with reference to certain embodiments thereof, it will be understood by those skilled in the art that various changes in form and details may be made therein without departing from the spirit and scope of the disclosure as defined by the appended claims and their equivalents.

What is claimed is:

1. A method for transmitting information by an electronic device, the method comprising:
   determining whether a body contact for human body communication is maintained based on a resistance measured through an electrode of the electronic device;
   in a case in which the body contact is maintained, determining whether an authentication message is received from a terminal, wherein the authentication message is received when the terminal determines that a comparison of first user identifiable information measured by the electronic device with second user identifiable information registered in the terminal meets a predetermined tolerance range;
   in a case in which the authentication message is received, determining whether a message that requests the information is received, wherein the message that requests the information indicates an operation mode including at least one of an exercise mode, a diet mode, an emotion managing mode, a treatment mode, or a management mode, and wherein the message that requests the information indicates a body condition to be measured;
   when the body contact is maintained and the message that requests the information is received, measuring the body condition, and transmitting, to the terminal, the information via the human body communication, wherein the information is based on the measured body condition; and
   when the body contact is not maintained, notifying a user that the body contact is not maintained.

2. The method of claim 1, further comprising:
   receiving, from the terminal, administration information based on the information.

3. An electronic device for transmitting information, the electronic device comprising:

an electrode unit including multiple electrodes for human body communication with a terminal and for measurement of a body condition; and a controller configured to:

determine whether a body contact for the human body communication is maintained based on a resistance measured through one of the multiple electrodes of the electrode unit;

in a case in which the body contact is maintained, determine whether an authentication message is received, wherein the authentication message is received when the terminal determines that a comparison of first user identifiable information measured by the electronic device with second user identifiable information registered in the terminal meets a predetermined tolerance range;

in a case in which the authentication message is received, determine whether a message that requests the information is received, wherein the message that requests the information indicates an operation mode including at least one of an exercise mode, a diet mode, an emotion managing mode, a treatment mode, or a management mode, and wherein the message that requests the information indicates the body condition to be measured;

when the body contact is maintained and the message that requests the information is received, measure the body condition, and transmit, to the terminal, the information via the human body communication, wherein the information is based on the measured body condition; and when the body contact is not maintained, notify a user that the body contact is not maintained.

4. The electronic device of claim 3, wherein the controller is further configured to receive, from the terminal, administration information based on the information.

5. A method for receiving information by a terminal, the method comprising:

determining whether a body contact for human body communication is maintained based on a resistance measured through an electrode of the terminal;

in a case in which the body contact is maintained, determining whether a comparison of first user identifiable information measured by an electronic device with second user identifiable information registered in the terminal meets a predetermined tolerance range;

in a case in which the comparison of the first user identifiable information with the second user identifiable information meets the predetermined tolerance range, sending an authentication message and a message requesting the information to the electronic device, wherein the message that requests the information indicates an operation mode including at least one of an exercise mode, a diet mode, an emotion managing mode, a treatment mode, or a management mode, and wherein the message that requests the information indicates a body condition to be measured;

when the body contact is maintained and the message that requests the information is sent, receiving the information via the human body communication, wherein the information is based on a measured body condition; and when the body contact is not maintained, notifying a user that the body contact is not maintained.

6. The method of claim 5, further comprising transmitting, to the electronic device, administration information based on the information.

7. A terminal for receiving information, the terminal comprising:

an electrode configured to perform human body communication with an electronic device; and a controller configured to:

determine whether a body contact for the human body communication is maintained based on a resistance measured through the electrode of the terminal;

in a case in which the body contact is maintained, determine whether a comparison of first user identifiable information measured by the electronic device with second user identifiable information registered in the terminal meets a predetermined tolerance range;

in a case in which the comparison of the first user identifiable information with the second user identifiable information meets the predetermined tolerance range, send an authentication message and a message requesting the information to the electronic device, wherein the message that requests the information indicates an operation mode including at least one of an exercise mode, a diet mode, an emotion managing mode, a treatment mode, or a management mode, and wherein the message that requests the information indicates a body condition to be measured;

when the body contact is maintained and the message that requests the information is sent, receive the information via the human body communication, wherein the information is based on a measured body condition; and when the body contact is not maintained, notify a user that the body contact is not maintained.

8. The terminal of claim 7, wherein the controller is further configured to transmit to the electronic device, administration information based on the information.

* * * * *